United States Patent [19]

Iwane et al.

[11] Patent Number: 5,091,592
[45] Date of Patent: Feb. 25, 1992

[54] PROCESS FOR PREPARING 4,4'-DIHYDROXYBIPHENYL

[75] Inventors: Hiroshi Iwane; Takahiro Sugawara; Kimiko Kaneko, all of Ibaraki, Japan

[73] Assignee: Mitsubishi Petrochemical Co., Ltd., Tokyo, Japan

[21] Appl. No.: 641,899

[22] Filed: Jan. 16, 1991

[30] Foreign Application Priority Data

Jan. 22, 1990 [JP] Japan .................................. 2-10674

[51] Int. Cl.$^5$ ........................ C07C 39/14; C07C 37/08
[52] U.S. Cl. ..................................................... 568/730
[58] Field of Search .............................. 568/730, 798

*Primary Examiner*—Werren B. Lone
*Attorney, Agent, or Firm*—Oblon, Spivak, McClelland, Maier & Neustadt

[57] ABSTRACT

A process for preparing 4,4'-dihydroxybiphenyl comprising oxidizing 4,4'-diisopropylbiphenyl with molecular oxygen and decomposing the resulting oxidation product in the presence of an acid catalyst is disclosed, in which oxidation of 4,4'-diisopropylbiphenyl is carried out in the presence of ammonia or an ammonium salt. The oxidation product has an increased selectivity of 4,4'-diisopropylbiphenyl dihydroperoxide and, therefore, produces the desired product in high yield upon acid decomposition.

12 Claims, No Drawings

PROCESS FOR PREPARING 4,4'-DIHYDROXYBIPHENYL

FIELD OF THE INVENTION

This invention relates to a process for preparing 4,4'-dihydroxybiphenyl (hereinafter abbreviated as BPL). More particularly, it relates to an improvement in a process for preparing BPL which comprises oxidizing 4,4'-diisopropylbiphenyl (hereinafter abbreviated as DIPBP) with molecular oxygen and decomposing the resulting peroxide in the presence of an acid catalyst.

BACKGROUND OF THE INVENTION

BPL is a compound useful as a material of liquid crystal polymers, heat-resistant resins, etc. Known processes for preparing BPL include a process comprising oxidatively coupling 2,6-di-t-butylphenol and reducing the resulting diphenoquinone for debutylation and a process comprising sulfonating biphenyl, followed by alkali fusion. These conventional processes have disadvantages in industrial application, such as complexity of steps involved and by-production of a large quantity of inorganic salts.

On the other hand, it is known that a dialkylbenzene is oxidized with molecular oxygen to obtain a corresponding hydroperoxide, which is then decomposed in the presence of an acid catalyst (acid decomposition) to obtain a phenol compound. For example, JP-A-48-72144 (the terms "JP-A" as used herein mean an "unexamined published Japanese patent application") discloses a process for preparing hydroquinone via p-diisopropylbenzene dihydroperoxide derived from p-diisopropylbenzene, and JP-A-61-93156 discloses a process for preparing 2,6-dihydroxynaphthalene via 2,6-diisopropylnaphthalene dihydroperoxide derived from 2,6-diisopropylnaphthalene.

JP-A-64-75440 discloses the process for preparing BPL via DIPBP, applied the above-described process, in which DIPBP is oxidized to obtain 4,4'-diisopropylbiphenyl dihydroperoxide (hereinafter abbreviated as DHP), which is then decomposed in the presence of an acid catalyst to obtain BPL.

The process of JP-A-64-75440 produces the following oxidation products including DHP.

| Product (abbreviation) | Structural Formula |
| --- | --- |
| DHP | 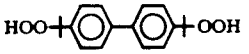 |
| 4-(2-Hydroxyisopropyl)-4'-(2-hydroperoxyisopropyl)biphenyl (HHP) | 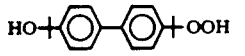 |
| 4,4'-Bis(2-hydroxyisopropyl)biphenyl (DCA) | 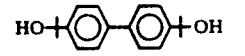 |
| 4-(2-Hydroperoxyisopropyl)-4'-isopropylbiphenyl (MHP) | 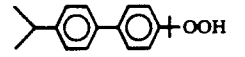 |
| 4-(2-Hydroxyisopropyl)-4'-isopropylbiphenyl (MCA) | 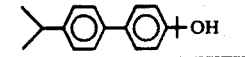 |

Of these oxidation products, HHP and DCA, when subjected to acid decomposition as such, produce no BPL but 4-(4-isopropenylphenyl)phenol or 4,4'-diisopropenylbiphenyl as dehydration products. Therefore, acid decomposition of HHP and DCA is carried out in the presence of 1 mole or more of hydrogen peroxide per mole of the 2-hydroxyisopropyl group to obtain BPL.

However, in the above-described process, when a conversion from DIPBP to DHP+HHP+DCA is increased in order to increase a yield of BPL, a production rate of DHP is decreased while those of HHP and DCA are increased. When, in particular, the oxidation reaction is performed until the proportion of substances with their isopropyl group remaining unreacted, such as MHP, MCA, and unreacted DIPBP, is reduced to 10% or less, the proportion of DHP in the oxidation product (DHP+HHP+DCA) becomes 35% or less. As a result, the amount of hydrogen peroxide to be added for acid decomposition should be increased in proportion to the increase of the 2-hydroxyisopropyl group.

Moreover, since oxidation reaction of DIPBP involves an induction period in its initial stage, the reaction must be conducted in the presence of a radical initiator.

SUMMARY OF THE INVENTION

An object of the present invention is to provide an industrially advantageous process for preparing BPL in high yield in which oxidation of DIPBP achieves an increased selectivity of DHP without requiring a radical initiator so that the subsequent acid decomposition can be accomplished with a reduced amount of hydrogen peroxide.

It has now been found that a selectivity of DHP in oxidation of DIPBP can be increased by adding ammonia or an ammonium salt to the oxidation system.

The present invention relates to a process for preparing BPL comprising oxidizing DIPBP with molecular oxygen and decomposing the resulting oxidation product in the presence of an acid catalyst, in which said oxidizing is carried out in the presence of ammonia or an ammonium salt.

DETAILED DESCRIPTION OF THE INVENTION

Oxidation of DIPBP with molecular oxygen is generally conducted in a basic aqueous solvent.

Where ammonia is added to the oxidation system, the system becomes basic so that the reaction sufficiently proceeds without addition of other basic compounds but, if desired, the reaction may be conducted in the co-presence of a basic compound, e.g., alkali metal compounds. Where an ammonium salt is added, the reaction is carried out in the co-presence of a basic compound, e.g., alkali metal compounds.

The basic compound, if used, preferably includes alkali metal compounds, such as alkali metal hydroxides, e.g., sodium hydroxide, potassium hydroxide, and lithium hydroxide; alkali metal carbonates, e.g., sodium carbonate and potassium carbonate; alkali metal bicarbonates, e.g., sodium hydrogencarbonate and potassium hydrogencarbonate; alkali metal phosphates, e.g., sodium phosphate, tribasic, potassium phosphate, tribasic, sodium phosphate, dibasic, potassium phosphate, dibasic, sodium phosphate, monobasic, and potassium phosphate, monobasic; and alkali metal borates, e.g., sodium tetraborate. These basic compounds may be used either individually or as a mixture of two or more thereof at an arbitrary mixing ratio. The amount of the alkali metal compounds added to an aqueous solvent is preferably at least 30% by weight based on water.

The basic aqueous solvent is used in an amount usually of from 0.1 to 10 parts, and preferably from 0.3 to 5 parts, by weight per part by weight of DIPBP. If the amount of the basic aqueous solvent is less than 0.1 part, oxidation does not sufficiently proceed. Even if it exceeds 10 parts, no further improvement is obtained, only resulting in an increase of a basic waste water.

Ammonia and ammonium salts which can be used in the oxidation reaction include ammonia gas, aqueous ammonia of arbitrary concentration, inorganic ammonium salts, e.g., ammonium sulfate, ammonium hydrochloride, ammonium nitrate, ammonium borate, ammonium bicarbonate, and ammonium hydrogensulfate, and organic ammonium salts, e.g., ammonium formate, ammonium acetate, ammonium citrate, monobasic, ammonium citrate, dibasic, and ammonium citrate, tribasic.

The amount of ammonia or an ammonium salt to be used ranges usually from 0.01 to 300 mol %, preferably from 0.1 to 150 mol %, and more preferably from 1 to 50 mol %, based on DIPBP. If it is less than 0.01 mol %, the expected effect cannot be produced. Amounts more than 300 mol % produce no further effects.

If desired, a surface active agent may be added to the preoxidation system. In this case, the surface active agent to be used is not particularly limited in kind and includes, for example, fatty acid soaps, alkylsulfonates, alkylbenzene or alkylnaphthalenesulfonates, alkyl ether sulfonates, alkyl phosphates, and alkyl ether phosphates. These surface active agents may be used either individually or in combination of two or more thereof at an arbitrary ratio.

The surface active agent is added in an amount usually of from 0.001 to 5%, and preferably from 0.01 to 2%, by weight based on DIPBP.

Molecular oxygen to be used for oxidation preferably includes oxygen gas and air. In using oxygen gas, it may be diluted with an inert gas, e.g., nitrogen, argon, and helium, to an arbitrary concentration.

In carrying out the oxidation reaction, DIPBP, ammonia or an ammonium salt and, if desired, a surface active agent are added to the above-described basic aqueous solvent, and molecular oxygen is supplied thereto with stirring. The reaction temperature is in the range of from 60° to 150° C., and preferably of from 80° to 130° C. At temperatures lower than 60° C., the reaction is seriously retarded. At temperatures higher than 150° C., decomposition of the hydroperoxide group is considerably accelerated. The reaction may be conducted under normal pressure or under pressure, but is preferably under pressure up to 10 kg/cm$^2$G. The reaction time is usually from 4 to 48 hours, though varying depending on the reaction temperature or whether a radical initiator is used or not.

The oxidation product obtained by the oxidation reaction is a mixture predominantly comprising DHP and containing, as by-products, HHP, DCA, MHP, MCA, etc.

The resulting oxidation product is collected by filtration, dissolved in an organic solvent, and then subjected to acid decomposition in the presence of an acid catalyst and hydrogen peroxide to obtain BPL.

Organic solvents which can be used for dissolving the oxidation product include ketones, e.g., acetone, methyl isobutyl ketone, and methyl ethyl ketone; lower alcohols, e.g., methanol and ethanol; ethers, e.g., diethyl ether, diisopropyl ether, and tetrahydrofuran; carboxylic acids, e.g., acetic acid and propionic acid; nitriles, e.g., acetonitrile; aromatic hydrocarbons, e.g., benzene, toluene, and xylene; aliphatic acyclic hydrocarbons, e.g., hexane, heptane, and isooctane; and alicyclic hydrocarbons, e.g., cyclopentane and cyclohexane. These solvents may be used either individually or in combination of two or more thereof at an arbitrary ratio.

Acid catalysts which can be used include inorganic acids, e.g., sulfuric acid, hydrochloric acid, nitric acid, and phosphoric acid; organic acids, e.g., trichloroacetic acid, p-toluenesulfonic acid, p-phenolsulfonic acid, and oxalic acid; heteropoly-acids, e.g., phosphomolybdic acid and phosphotungstic acid; and solid acid catalysts, e.g., strongly acidic ion exchange resins, active clay, silica-alumina, and zeolite.

The acid catalyst is used in an amount of from 0.01 to 20%, and preferably from 0.1 to 10%, by weight based on the oxidation product.

Hydrogen peroxide is used for oxidation of HHP and DCA of the oxidation products to DHP to thereby increase a yield of BPL. Use of hydrogen peroxide is also advantageous in that dehydrating condensation of carbinols can be markedly inhibited.

Hydrogen peroxide to be used includes not only hydrogen peroxide itself and its aqueous solution but precursors capable of producing hydrogen peroxide under conditions of acid decomposition, such as sodium peroxide and calcium peroxide, with aqueous hydrogen peroxide, particularly in a concentration of from 5 to 70% by weight, being preferred.

Hydrogen peroxide is used in an amount of from 1 to 2 mols, and preferably from 1 to 1.5 mols, per mol of the total 2-hydroxyisopropyl groups in HHP, DCA, MCA, etc.

The acid decomposition reaction is carried out by heating an organic solvent having dissolved therein the oxidation product in the presence of hydrogen peroxide and the above-described acid catalyst. The reaction temperature is from 10° to 120° C., and preferably from 20° to 100° C. The reaction time, though depending on the reaction temperature, usually ranges from 0.5 to 12 hours, and preferably from 1 to 8 hours.

After completion of the reaction, a base is added to the reaction mixture to neutralize the acid catalyst, and the aqueous layer is separated. The organic solvent is recovered from the organic layer to obtain a desired product.

The present invention is now illustrated in greater detail with reference to Examples and Comparative Examples, but it should be understood that the present invention is not deemed to be limited thereto. All the percents, parts, and ratios are by weight unless otherwise indicated.

Yields of the products obtained are expressed in terms of mol % based on the starting DIPBP. That is, $$\text{Yield} = \frac{\text{Number of Moles of Product}}{\text{Number of Moles of DIPBP Charged}} \times 100(\%)$$

Analyses and quantitative determinations were made by high performance liquid chromatography.

EXAMPLE 1

In a 50 ml autoclave made of Hastelloy B were charged 5.0 g (21.0 mmol) of DIPBP, 15.0 g of a 0.2% aqueous sodium hydroxide solution, 0.11 g (1.64 mmol) of 25% aqueous ammonia, and, as a surface active agent, 0.025 g of Nonsal LN-1 (a trade name of a mixture of aliphatic carboxylic acid sodium salts, produced by Nippon Oils & Fats Co., Ltd.).

Oxygen was introduced under a gauge pressure of 2 kg/cm$^2$ to conduct oxidation at 100° C. for 12 hours while stirring at 1500 rpm. During the reaction, oxygen was continuously fed so as to maintain the reaction pressure at 2 kg/cm$^2$G.

The conversion of DIPBP was 99.6%; the yields of DHP, HHP, and DCA were 51.1%, 27.7%, and 3.8%, respectively; the selectivity of DHP in (DHP+HHP+DCA) was 61.9%; and the yields of MHP and MCA were 8.0% and 2.2%, respectively.

The oxidation reaction mixture was filtered, washed with water and dried to recover 6.5 g of the oxidation product. The oxidation product (6.5 g) was dissolved in 20 g of acetone, and 1.07 g (9.7 mmol) of 30% aqueous hydrogen peroxide was added thereto to prepare a uniform acetone solution A. The amount of hydrogen peroxide added corresponded to 1.2 mole-equivalent based on the 2-hydroxyisopropyl group in the oxidation product.

Three grams of acetone were charged in a 100 ml four-necked flask equipped with a reflux condenser and a thermometer and heated to 50° C. Separately, a solution of 0.31 g of 97% sulfuric acid in 5 g of acetone was prepared (designated acetone solution B). Acetone solutions A and B were separately fed to the flask in a continuous manner using a respective pump over a period of 1.5 hours. After completion of the feeding, the reaction was further continued for an additional period of 1.5 hours.

The reaction mixture was adjusted to a pH of 6 by addition of a 5% aqueous sodium hydroxide solution, and the aqueous layer was separated. Acetone was recovered from the organic layer to obtain 4.2 g of a pale yellow solid. The solid was found to contain 3.22 g of BPL. The conversions of DHP, HHP, and DCA were all 100%, and the yield of BPL was 82.3%.

EXAMPLE 2

DIPBP was oxidized for 12 hours under the same conditions as in Example 1, except for replacing 25% aqueous ammonia with 0.11 g (0.84 mmol) of ammonium sulfate.

The conversion of DIPBP was 99.1%. The yields of DHP, HHP, and DCA were 49.7%, 28.9%, and 4.5%, respectively, and the selectivity of DHP in (DHP+HHP+DCA) was 59.8%. 7.7% of MHP and 2.7% of MCA were by-produced.

The oxidation reaction mixture was filtered, washed with water, dried, and then subjected to acid decomposition under the same conditions as in Example 1, except for changing the amount of the 30% aqueous hydrogen peroxide to 1.16 g (10.2 mmol) which corresponded to 1.2 mol-equivalent based on the total 2-hydroxyisopropyl group in the oxidation product.

As a result, there was obtained 4.1 g of a pale yellow solid containing 3.25 g of BPL. The conversions of DHP, HHP, and DCA were all 100%, and the yield of BPL was 83.1%.

COMPARATIVE EXAMPLE 1

Oxidation of DIPBP was carried out under the same conditions as in Example 1, except that ammonia was not added, and 0.2 ml of a 5.0% aqueous sodium hydroxide solution was added to the reaction system at an interval of 2 hours. The reaction was continued for 26 hours.

The conversion of DIPBP was 98.6%. The yields of DHP, HHP, and DCA were 40.7%, 25.1%, and 2.9%, respectively, and the selectivity of DHP in (DHP+HHP+DCA) was 59.2%. 15.3% of MHP and 6.4% of MCA were by-produced.

The oxidation reaction mixture was filtered, washed with water, dried, and then subjected to acid decomposition under the same conditions as in Example 1, except for changing the amount of the 30% aqueous hydrogen peroxide to 1.06 g (9.40 mmol), which corresponded to 1.2 mol-equivalent to the total 2-hydroxyisopropyl groups in the oxidation product.

As a result, there was obtained 4.40 g of a pale yellow solid containing 2.68 g of BPL. The conversions of DHP, HHP, and DCA were all 100%, and the yield of BPL was 68.4%.

COMPARATIVE EXAMPLE 2

Oxidation of DIPBP was carried out for 42 hours under the same conditions as in Example 1, except for adding neither ammonia nor a surface active agent and replacing the 0.5% aqueous sodium hydroxide solution with 10 g of a 4.5% aqueous sodium hydroxide solution.

The conversion of DIPBP was 99.8%, and the yields of DHP, HHP, and DCA were 6.6%, 40.3%, and 36.2%, respectively, with the selectivity of DHP in (DHP+HHP+DCA) being 7.9%. 2.5% of MHP and 6.7% of MCA were by-produced.

The oxidation reaction mixture was filtered, washed with water, dried, and then subjected to acid decomposition under the same conditions as in Example 1, except for changing the amount of the 30% aqueous hydrogen peroxide to 3.41 g (30.1 mmol), which corresponded to 1.2 mol-equivalent to the total 2-hydroxyisopropyl groups in the oxidation product.

As a result, there was obtained 4.11 g of a pale yellow solid containing 3.25 g of BPL. The conversions to DHP, HHP, and DCA were all 100%, and the yield of BPL was 83.1%.

As described above, according to the process of the present invention in which oxidation of DIPBP is carried out in the presence of ammonia or an ammonium salt, a selectivity of DHP can be increased and, as a result, the subsequent acid decomposition produces BPL in high yield.

While the invention has been described in detail and wit reference to specific examples thereof, it will be apparent to one skilled in the art that various changes and modifications can be made therein without departing from the spirit and scope thereof.

What is claimed is:

1. A process for preparing 4,4'-dihydroxybiphenyl comprising oxidizing 4,4'-diisopropylbiphenyl with molecular oxygen in a basic aqueous solvent and decomposing the resulting oxidation product in the presence of an acid catalyst, selected from inorganic acid, organic acid, heteropoly-acid and solid acid catalyst, in which said oxidizing is carried out in the presence of ammonia or an ammonium salt.

2. A process as claimed in claim 1, wherein said ammonium salt is an inorganic ammonium salt.

3. A process as claimed in claim 1, wherein said ammonia or ammonium salt is present in an amount of from 0.01 to 300 mol % based on 4,4'-diisopropylbiphenyl.

4. A process as claimed in claim 1, wherein said oxidizing is carried out in the presence of an alkali metal compound.

5. A process as claimed in claim 1, wherein said oxidizing is carried out in the presence of a surface active agent.

6. A process as claimed in claim 5, wherein said surface active agent is present in an amount of from 0.001 to 5% by weight based on 4,4'-diisopropylbiphenyl.

7. A process as claimed in claim 1, wherein said oxidizing is at a temperature of from 60° to 150° C.

8. A process as claimed in claim 1, wherein said oxidizing is under a pressure of from normal pressure to 10 kg/cm$^2$G.

9. A process as claimed in claim 1, wherein said inorganic acid is selected from the group consisting of sulfuric acid, hydrochloric acid, nitric acid and phosphoric acid.

10. A process as claimed in claim 1, wherein said organic acid is selected from the group consisting of trichloroacetic acid, p-toluenesulfonic acid, p-phenolsulfonic acid, and oxalic acid.

11. A process as claimed in claim 1, wherein said heteropoly-acid is selected from the group consisting of phosphomolybdic acid and phosphotungstic acid.

12. A process as claimed in claim 1, wherein said solid acid catalyst is selected from the group consisting of strongly acidic ion exchange resins, active clay, silica-alumina, and zeolite.

* * * * *